(12) United States Patent
Ishizaki et al.

(10) Patent No.: US 11,931,498 B2
(45) Date of Patent: Mar. 19, 2024

(54) BLOOD PURIFICATION APPARATUS

(71) Applicant: Nikkiso Company Limited, Tokyo (JP)

(72) Inventors: Fumihiko Ishizaki, Shizuoka (JP);
Sumiaki Matsuo, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 794 days.

(21) Appl. No.: 16/716,880

(22) Filed: Dec. 17, 2019

(65) Prior Publication Data

US 2020/0121844 A1 Apr. 23, 2020

Related U.S. Application Data

(63) Continuation of application No. PCT/JP2018/023480, filed on Jun. 20, 2018.

(30) Foreign Application Priority Data

Jun. 20, 2017 (JP) ................................. 2017-120203

(51) Int. Cl.
*A61M 1/16* (2006.01)
*A61M 1/30* (2006.01)
(Continued)

(52) U.S. Cl.
CPC ........ *A61M 1/3448* (2014.02); *A61M 1/1645* (2014.02); *A61M 1/306* (2014.02); *B01D 61/32* (2013.01); *A61M 2202/0021* (2013.01)

(58) Field of Classification Search
CPC .... H02K 1/146; H02K 1/165; H02K 2213/03; H02K 3/325; H02K 3/345; A61M 1/1601;
(Continued)

(56) References Cited

U.S. PATENT DOCUMENTS 4,747,950 A 5/1988 Guinn
4,834,888 A * 5/1989 Polaschegg ........... A61M 1/165
210/741

(Continued)

FOREIGN PATENT DOCUMENTS

DE 10100146 A1 7/2002
DE 102014003619 A1 9/2015
(Continued)

OTHER PUBLICATIONS

English Translation of Ueda et al Patent Publication JP2016005524A, published Jan. 2016. (Year: 2016).*

(Continued)

*Primary Examiner* — Joseph W Drodge
(74) *Attorney, Agent, or Firm* — Young Basile Hanlon & MacFarlane, P.C.

(57) ABSTRACT

A blood purification apparatus is provided in which waste liquid is prevented from flowing through an ultrafiltration pump during ultrafiltration so that the performance and accuracy of ultrafiltration can be maintained over a long period. The blood purification apparatus includes an ultrafiltration line one end of which is connected to a dialysate introduction line at a position on a downstream side with respect to a duplex pump. The ultrafiltration line is provided with the ultrafiltration pump. The ultrafiltration pump is capable of performing ultrafiltration by drawing dialysate in the dialysate introduction line through the ultrafiltration line such that the volume of the dialysate to be introduced into a dialyzer becomes smaller than the volume of waste liquid to be drained from the dialyzer.

17 Claims, 8 Drawing Sheets

(51) Int. Cl.
*A61M 1/34* (2006.01)
*B01D 61/32* (2006.01)

(58) Field of Classification Search
CPC .. A61M 1/1641; A61M 1/1645; A61M 1/306; A61M 1/3403; A61M 1/3448; A61M 2202/0021; A61M 2205/07; A61M 2205/3337; A61M 2205/3355; A61M 2205/3365; A61M 1/1603; A61M 1/1647; A61M 1/1654; A61M 1/1656; A61M 1/1657; B01D 61/30; B01D 61/32
See application file for complete search history.

(56) References Cited

U.S. PATENT DOCUMENTS

| | | | |
|---|---|---|---|
| 5,589,070 A * | 12/1996 | Maltais | A61M 1/1684 134/22.12 |
| 2013/0020237 A1 * | 1/2013 | Wilt | G16H 20/40 210/85 |
| 2013/0037485 A1 * | 2/2013 | Wilt | A61M 1/166 210/85 |
| 2013/0150768 A1 * | 6/2013 | Sakamoto | A61M 1/1601 73/40.5 R |
| 2016/0058933 A1 * | 3/2016 | Ballantyne | G06F 21/565 210/85 |
| 2016/0136346 A1 * | 5/2016 | Cho | A61M 1/1641 210/136 |
| 2017/0326282 A1 * | 11/2017 | Wilt | A61M 1/362265 |

FOREIGN PATENT DOCUMENTS

| | | | | |
|---|---|---|---|---|
| JP | H02-118553 U | 9/1990 | | |
| JP | H07-080060 A | 3/1995 | | |
| JP | 2000-325470 A | 11/2000 | | |
| JP | 2010-131146 A | 6/2010 | | |
| JP | 2010-136746 A | 6/2010 | | |
| JP | 2016005524 A * | 1/2016 | | A61M 1/14 |
| WO | WO8300725 A1 * | 3/1983 | | |
| WO | WO-2017062921 A1 * | 4/2017 | | A61M 1/10 |

OTHER PUBLICATIONS

European Search Report for Application No. 18821565.1, dated Mar. 4, 2021.

* cited by examiner

BLOOD PURIFICATION APPARATUS

CROSS-REFERENCE TO RELATED APPLICATION(S)

This application is a continuation of International Application No. PCT/JP2018/023480, filed on Jun. 20, 2018, which claims priority to Japanese Application No. 2017-120203, filed on Jun. 20, 2017, the entire disclosures of which are hereby incorporated by reference.

FIELD

The present invention relates to a blood purification apparatus for performing purification treatment and ultrafiltration while causing blood of a patient to extracorporeally circulate.

BACKGROUND

In general, a blood purification apparatus for performing blood purification treatment (dialysis treatment) includes a blood circuit for causing blood of a patient to extracorporeally circulate, a dialyzer connected to a halfway position of the blood circuit, a peristaltic blood pump, a dialysate introduction line through which dialysate can be introduced into the dialyzer, a dialysate drain line through which waste liquid generated from the dialyzer can be drained, a liquid-delivering pump capable of delivering liquid such that the volume of the dialysate to be introduced into the dialyzer and the volume of the waste liquid to be drained from the dialyzer are substantially equalized, a bypass line that bypasses the liquid-delivering pump provided to the dialysate drain line, and an ultrafiltration pump provided to the bypass line and intended for removal of water from the blood of the patient (see PTL 1, for example).

When the blood pump is activated with puncture needles at the respective distal ends of the blood circuit being stuck in the patient, blood of the patient extracorporeally circulates through the blood circuit and is purified by the dialyzer. Furthermore, when the ultrafiltration pump is activated, the volume of the waste liquid to be drained from the dialyzer becomes greater than the volume of the dialysate to be introduced into the dialyzer. Therefore, not only the waste liquid but also water removed from the blood of the patient is drained. Thus, ultrafiltration can be implemented.

PTL 1: Japanese Unexamined Patent Application Publication No. 2010-136746, the teachings of which are incorporated by reference herein for all purposes.

SUMMARY

However, since the ultrafiltration pump of the above known blood purification apparatus is provided to the bypass line connected to the dialysate drain line, not only the water but also the waste liquid flows through the ultrafiltration pump during ultrafiltration. Consequently, waste products such as protein contained in the waste liquid may adhere to the pump chamber of the ultrafiltration pump. If the apparatus under such a condition is used for a long period, the capacity of the pump chamber changes, making it difficult to control the volume of ultrafiltration. Therefore, scrubbing typically needs to be performed to remove the waste products such as protein for accuracy maintenance.

The present invention has been conceived in view of the above circumstances and provides a blood purification apparatus in which waste liquid is prevented from flowing through an ultrafiltration pump during ultrafiltration so that the performance and accuracy of ultrafiltration can be maintained over a long period.

According to the teachings herein, there is provided a blood purification apparatus including a blood circuit including an arterial blood circuit and a venous blood circuit and through which blood of a patient is allowed to extracorporeally circulate, a blood purification device connected to the arterial blood circuit and to the venous blood circuit and that purifies the blood flowing through the blood circuit, a dialysate introduction line that allows dialysate to be introduced into the blood purification device, a dialysate drain line that allows waste liquid to be drained from the blood purification device, a liquid-delivering device capable of delivering liquid such that a volume of the dialysate to be introduced into the blood purification device and a volume of the waste liquid to be drained from the blood purification device are substantially equalized, and an ultrafiltration pump capable of removing, through the blood purification device, water from the blood flowing through the blood circuit. The blood purification apparatus includes an ultrafiltration line one end of which is connected to the dialysate introduction line at a position on a downstream side with respect to the liquid-delivering device. The ultrafiltration line is provided with an ultrafiltration pump. The ultrafiltration pump is capable of performing ultrafiltration by drawing the dialysate in the dialysate introduction line through the ultrafiltration line such that the volume of the dialysate to be introduced into the blood purification device becomes smaller than the volume of the waste liquid to be drained from the blood purification device.

According to the teachings herein, in the blood purification apparatus taught herein, an other end of the ultrafiltration line is connected to the dialysate introduction line at a position on an upstream side with respect to the liquid-delivering device.

According to the teachings herein, in the blood purification apparatus taught herein, an other end of the ultrafiltration line is connected to the dialysate drain line at a position on a downstream side with respect to the liquid-delivering device.

According to the taught herein, in the blood purification apparatus taught herein, ultrafiltration is performable without introducing the dialysate into the blood purification device if the liquid-delivering device and the ultrafiltration pump are operated such that a volume of liquid delivery by the liquid-delivering device and a volume of liquid delivery by the ultrafiltration pump are substantially equalized.

According to the teachings herein, in the blood purification apparatus taught herein, the liquid-delivering device and the ultrafiltration pump are each a pump capable of delivering liquid by periodically undergoing a suction step of taking in the liquid and a discharge step of discharging the taken liquid. Furthermore, the ultrafiltration pump operates only in a period where the liquid-delivering device is undergoing the discharge step.

According to the teachings herein, in the blood purification apparatus taught herein, the ultrafiltration pump operates on condition that a pressure of liquid discharge in the discharge step undergone by the liquid-delivering device exceeds a predetermined value.

According to the teachings herein, in the blood purification apparatus taught herein, the blood purification apparatus includes a synchronization device capable of synchronizing the suction step and the discharge step undergone by the liquid-delivering device and the ultrafiltration pump such that the ultrafiltration pump undergoes the suction step while the liquid-delivering device is undergoing the discharge step, and the ultrafiltration pump undergoes the discharge step while the liquid-delivering device is undergoing the suction step.

According to the taught herein, in the blood purification apparatus taught herein, the liquid-delivering device or the ultrafiltration pump is a pump capable of delivering liquid by periodically undergoing a suction step of taking in the liquid and a discharge step of discharging the taken liquid, and is capable of delivering the liquid while maintaining a volume of liquid discharge in the discharge step at a predetermined level by increasing a pressure of liquid discharge in an early stage and in a late stage of the discharge step while reducing the pressure of liquid discharge in an intermediate stage between the two stages.

According to the teachings herein, in the blood purification apparatus taught herein, the liquid-delivering device is a duplex pump that includes a supply-side pump chamber connected to the dialysate introduction line and being capable of accommodating and discharging the dialysate from and into the dialysate introduction line, and a drain-side pump chamber connected to the dialysate drain line and being capable of taking in and accommodating the waste liquid from the dialysate drain line. Furthermore, the liquid-delivering device delivers the liquid such that a volume of discharge from the supply-side pump chamber and a volume of suction into the drain-side pump chamber are substantially equalized. Furthermore, one end of the ultrafiltration line is connected to the dialysate introduction line at a position between the supply-side pump chamber and a point of connection of the dialysate introduction line to the blood purification device.

According to the teachings herein, the ultrafiltration pump is capable of performing ultrafiltration by drawing the dialysate in the dialysate introduction line through the ultrafiltration line such that the volume of the dialysate to be introduced into the blood purification device becomes smaller than the volume of the waste liquid to be drained from the blood purification device. Therefore, the waste liquid is prevented from flowing through the ultrafiltration pump during ultrafiltration so that the performance and accuracy of ultrafiltration can be maintained over a long period.

According to teachings herein, the other end of the ultrafiltration line is connected to the dialysate introduction line at the position on the upstream side with respect to the liquid-delivering device. Therefore, the dialysate drawn through the ultrafiltration line during ultrafiltration can be returned to the dialysate introduction line. Thus, the dialysate can be used efficiently.

According to the teachings herein, the other end of the ultrafiltration line is connected to the dialysate drain line at the position on the downstream side with respect to the liquid-delivering device. Therefore, the dialysate drawn through the ultrafiltration line during ultrafiltration can be drained to the outside of the apparatus through the dialysate drain line.

According to the teachings herein, ultrafiltration is performable without introducing the dialysate into the blood purification device if the liquid-delivering device and the ultrafiltration pump are operated such that the volume of liquid delivery by the liquid-delivering device and the volume of liquid delivery by the ultrafiltration pump are substantially equalized. Therefore, while the waste liquid is prevented from flowing through the ultrafiltration pump so that the performance and accuracy of ultrafiltration can be maintained over a long period, ultrafiltration alone can be performed without introducing the dialysate into the blood purification device.

According to the teachings herein, the liquid-delivering device and the ultrafiltration pump are each a pump capable of delivering liquid by periodically undergoing the suction step of taking in the liquid and the discharge step of discharging the taken liquid. Furthermore, the ultrafiltration pump operates only in a period where the liquid-delivering device is undergoing the discharge step. Therefore, activation of the ultrafiltration pump while the liquid-delivering device is undergoing the suction step can be assuredly avoided. Accordingly, the dialysate introduced into the blood purification device can be prevented from flowing backward into the dialysate introduction line.

According to the teachings herein, the ultrafiltration pump operates on condition that the pressure of liquid discharge in the discharge step undergone by the liquid-delivering device exceeds a predetermined value. Therefore, the dialysate introduced into the blood purification device can be more assuredly prevented from flowing backward into the dialysate introduction line.

According to the teachings herein, the blood purification apparatus includes a synchronization device capable of synchronizing the suction step and the discharge step undergone by the liquid-delivering device and the ultrafiltration pump such that the ultrafiltration pump undergoes the suction step while the liquid-delivering device is undergoing the discharge step, and the ultrafiltration pump undergoes the discharge step while the liquid-delivering device is undergoing the suction step. Therefore, the ultrafiltration pump can be assuredly prevented from undergoing the discharge step while the liquid-delivering device is undergoing the suction step. Accordingly, the dialysate introduced into the blood purification device can be much more assuredly prevented from flowing backward into the dialysate introduction line.

According to the teachings herein, the liquid-delivering device or the ultrafiltration pump is a pump capable of delivering liquid by periodically undergoing the suction step of taking in the liquid and the discharge step of discharging the taken liquid, and is capable of delivering the liquid while maintaining the volume of liquid discharge in the discharge step at a predetermined level by increasing the pressure of liquid discharge in the early stage and in the late stage of the discharge step while reducing the pressure of liquid discharge in the intermediate stage between the two stages. Such a configuration can reduce the probability that the ultrafiltration pump may undergo the suction step while the discharge pressure in the discharge step undergone by the liquid-delivering device is low. Accordingly, the probability that the dialysate introduced into the blood purification device flows backward into the dialysate introduction line can be reduced.

According to the teachings herein, the liquid-delivering device is the duplex pump that includes the supply-side pump chamber connected to the dialysate introduction line and being capable of accommodating and discharging the dialysate from and into the dialysate introduction line, and the drain-side pump chamber connected to the dialysate drain line and being capable of taking in and accommodating the waste liquid from the dialysate drain line. Furthermore, the liquid-delivering device delivers the liquid such that the volume of discharge from the supply-side pump chamber and the volume of suction into the drain-side pump chamber are substantially equalized. Furthermore, one end of the ultrafiltration line is connected to the dialysate introduction line at the position between the supply-side pump chamber and the point of connection of the dialysate introduction line to the blood purification device. Therefore, while the dialysate and the waste liquid are delivered by the liquid-delivering device, the waste liquid is prevented from flowing through the ultrafiltration pump during ultrafiltration so that the performance and accuracy of ultrafiltration can be maintained over a long period.

DETAILED DESCRIPTION

Embodiments of the present invention will now be described specifically with reference to the drawings.

Figure 1:
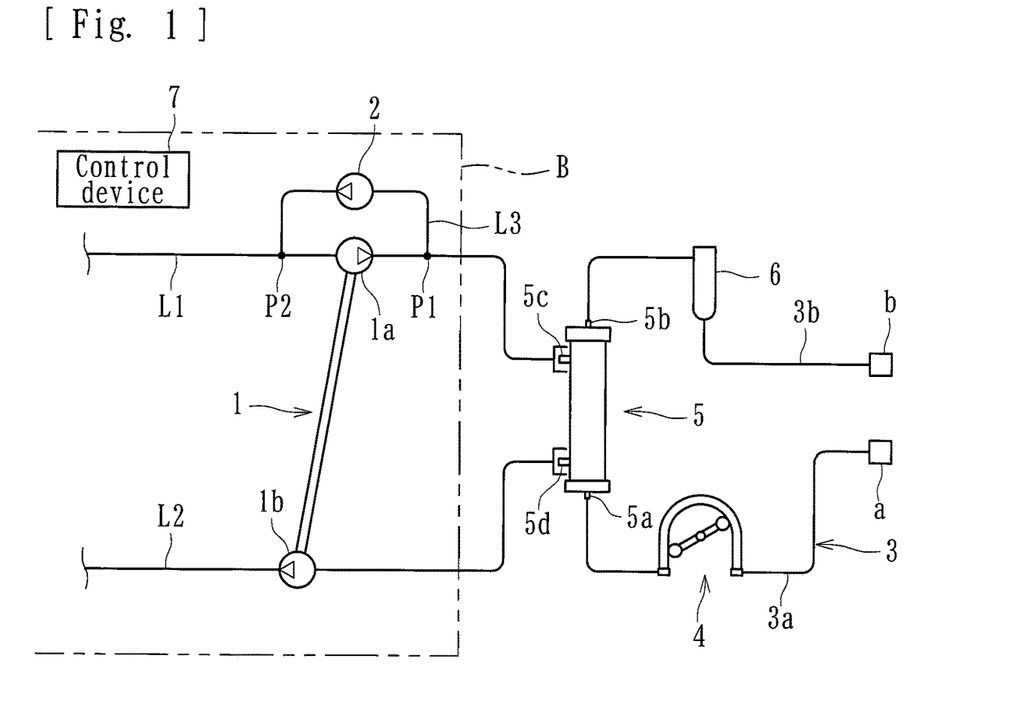
FIG. 1 is a diagram illustrating a blood purification apparatus according to a first embodiment of the present invention.

A blood purification apparatus according to a first embodiment is applied to a hemodialysis apparatus and basically includes, as illustrated in FIG. 1, a blood circuit 3 (including an arterial blood circuit 3*a* and a venous blood circuit 3*b*) connected to a dialyzer 5 (a blood purification device), and an apparatus body B including a duplex pump 1 (a liquid-delivering device), an ultrafiltration pump 2, a control device 7, a dialysate introduction line L1, a dialysate drain line L2, and an ultrafiltration line L3.

The dialyzer 5 has thereinside blood purification membranes, not illustrated (the present embodiment employs hollow-fiber hemodialysis membranes or hemodiafiltration membranes, but flat hemodialysis membranes are also acceptable). The dialyzer 5 further has a blood inlet 5*a* from which blood is introduced thereinto, a blood outlet 5*b* from which the blood introduced is discharged, a dialysate inlet 5*c* from which dialysate is introduced thereinto, and a dialysate outlet 5*d* from which the dialysate introduced is discharged. The blood introduced from the blood inlet 5*a* is brought into contact with the dialysate through the hollow-fiber membranes and is thus purified.

The arterial blood circuit 3*a* is basically formed of a flexible tube, with one end thereof being connected to the blood inlet 5*a* of the dialyzer 5, whereby the blood collected from the blood vessel of the patient is introduced into the hollow-fiber membranes provided in the dialyzer 5. The arterial blood circuit 3*a* is provided with an arterial puncture needle a at the other end thereof, and a blood pump 4. The blood pump 4 according to the present embodiment is a peristaltic pump.

As with the arterial blood circuit 3*a*, the venous blood circuit 3*b* is basically formed of a flexible tube, with one end thereof being connected to the blood outlet 5*b* of the dialyzer 5, whereby the blood having flowed through the hollow-fiber membranes is discharged. The venous blood circuit 3*b* is provided with a venous puncture needle (b) at the other end thereof, and an air-trap chamber 6 for bubble removal at a halfway position thereof. Hence, the blood of the patient collected through the arterial puncture needle a flows through the arterial blood circuit 3*a* to the dialyzer 5 and is purified therein. Then, the blood flows through the venous blood circuit 3*b* and is returned into the body of the patient through the venous puncture needle (b).

As described above, the blood of the patient extracorporeally circulates through the blood circuit 3. In this process, blood purification treatment is performed with the dialyzer 5. In this specification, the side of the puncture needle provided for blood removal (blood collection) is referred to as the "arterial" side, and the side of the puncture needle provided for blood return is referred to as the "venous" side. The "arterial" side and the "venous" side are not defined in accordance with which of the artery and the vein is to be the object of puncture.

The dialysate inlet 5*c* and the dialysate outlet 5*d* of the dialyzer 5 receive the respective ends of the dialysate introduction line L1 and the dialysate drain line L2 connected thereto, whereby the dialysate introduced into the dialyzer 5 through the dialysate introduction line L1 is allowed to flow outside the hollow-fiber membranes and to be drained through the dialysate drain line L2 together with waste liquid. That is, the dialysate introduction line L1 allows the dialysate to be introduced into the dialyzer 5, whereas the dialysate drain line L2 allows the waste liquid to be drained from the dialyzer 5.

The apparatus body B includes not only the dialysate introduction line L1 and the dialysate drain line L2 but also the duplex pump 1, the ultrafiltration pump 2, and so forth. The duplex pump 1 is provided over the dialysate introduction line L1 and the dialysate drain line L2. When activated, the duplex pump 1 causes the dialysate, prepared to have a predetermined concentration, to flow into the dialyzer 5 and the waste liquid to be drained from the dialyzer 5. The duplex pump 1 may be replaced with a liquid-delivering device of another type (such as a liquid-delivering device including a balance chamber) capable of delivering the dialysate in the dialysate introduction line L1 to the dialyzer 5 while draining the waste liquid from the dialyzer 5.

Figure 3:
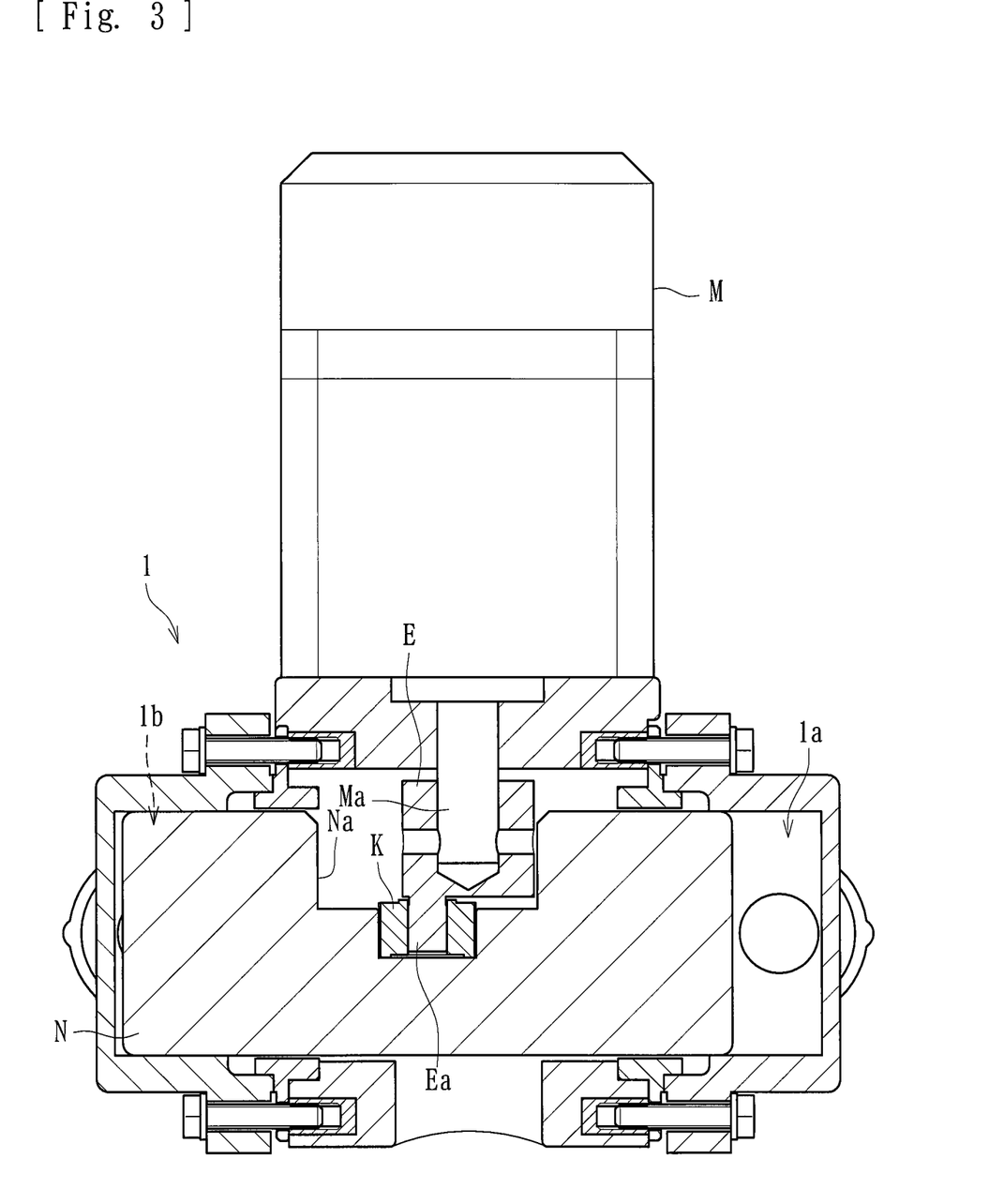
FIG. 3 is a vertical sectional view of a duplex pump (liquid-delivering device) applied to the first and second embodiments of the present invention.
Figure 4:
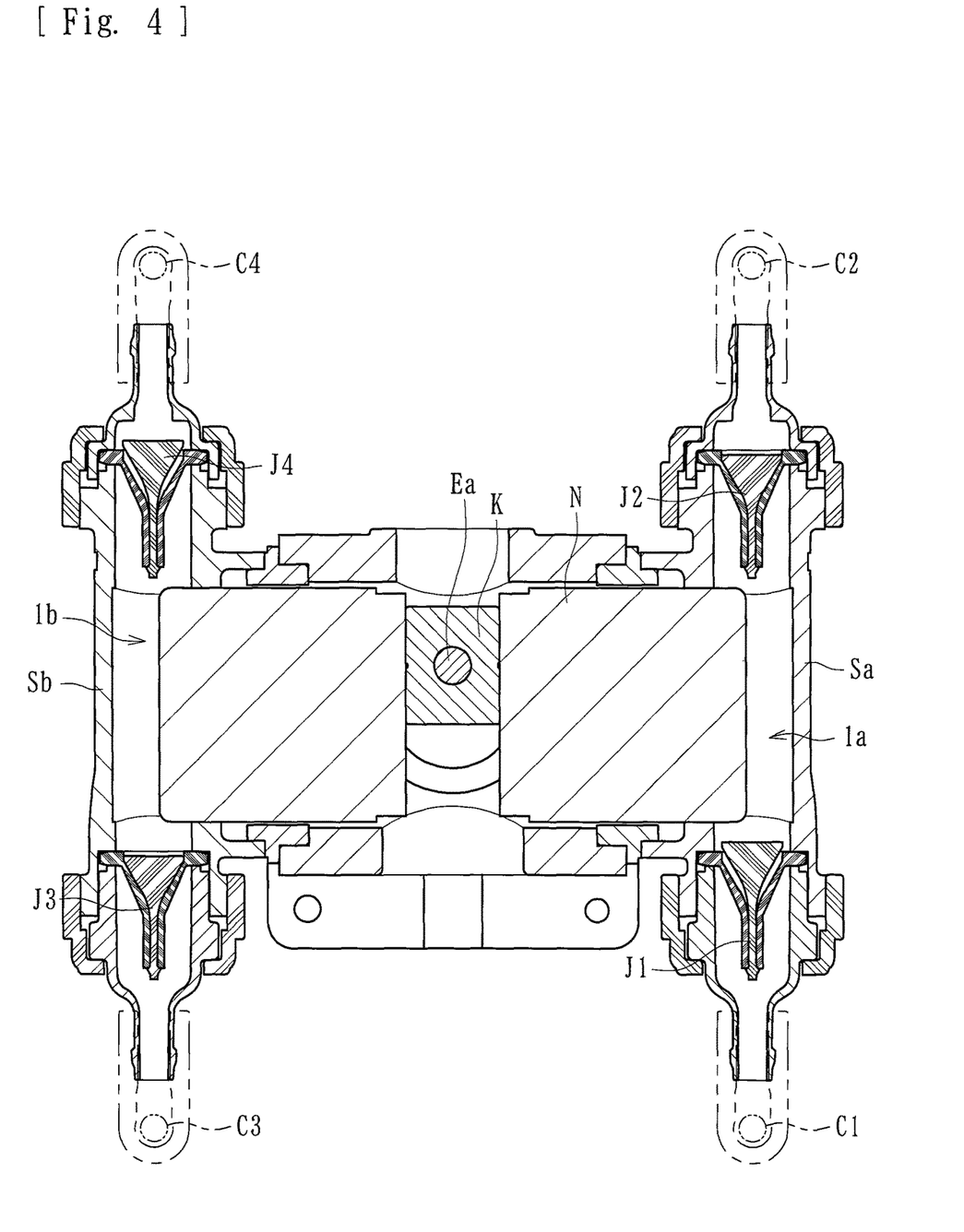
FIG. 4 is a horizontal sectional view of the duplex pump (liquid-delivering device).

More specifically, the duplex pump 1 according to the present embodiment is a pump capable of delivering liquid such that the volume of the dialysate to be introduced into the dialyzer 5 and the volume of the waste liquid to be drained from the dialyzer 5 are substantially equalized. As illustrated in FIGS. 3 and 4, the duplex pump 1 includes a supply-side pump chamber 1a, a drain-side pump chamber 1b, a supply-side suction port C1 from which the dialysate is allowed to be taken into the supply-side pump chamber 1a, a supply-side discharge port C2 from which the dialysate in the supply-side pump chamber 1a is allowed to be discharged, a drain-side suction port C3 from which the dialysate is allowed to be taken into the drain-side pump chamber 1b, a drain-side discharge port C4 from which the dialysate in the drain-side pump chamber 1b is allowed to be discharged, a motor (M), a plunger (N), and check valves (J1 to J4).

The supply-side pump chamber 1a is an accommodation space having a predetermined capacity and allows, with a reciprocating motion of the plunger (N), the dialysate taken therein from the supply-side suction port C1 to flow therethrough and to be discharged from the supply-side discharge port C2. The drain-side pump chamber 1b is also an accommodation space having a predetermined capacity and allows, with the reciprocating motion of the plunger (N), the dialysate taken therein from the drain-side suction port C3 to flow therethrough and to be discharged from the drain-side discharge port C4. The supply-side suction port C1 and the supply-side discharge port C2 are connected to a pipe forming the dialysate introduction line L1. The drain-side suction port C3 and the drain-side discharge port C4 are connected to a pipe forming the dialysate drain line L2.

The plunger (N) is reciprocatable by the motor (M) with respect to the supply-side pump chamber 1a and the drain-side pump chamber 1b. The plunger (N) undergoing the reciprocating motion takes the dialysate into the supply-side pump chamber 1a and into the drain-side pump chamber 1b from the supply-side suction port C1 and from the drain-side suction port C3 respectively, and discharges the thus taken dialysate from the supply-side discharge port C2 and from the drain-side discharge port C4 respectively, thereby delivering the dialysate.

An output shaft (Ma) of the motor (M) is provided with a cam member (E). The cam member (E) has a cam portion (Ea) projecting at a position different from the axis of the output shaft (Ma) (at a position decentered from the center of rotation). With the motor (M) and relevant elements being assembled together, the cam member (E) is positioned in a recess (Na) provided in the plunger (N). The cam portion (Ea) is provided with a block slider (K). When the motor (M) is activated, the block slider (K) pushes the plunger (N) in the lengthwise direction and thus causes the plunger (N) to reciprocate in the lateral direction in FIG. 3.

The check valves (J1 and J2) are each a valve having a function of preventing the backflow of the dialysate by keeping the dialysate flowing in one specific direction. The check valves (J1 and J2) are each provided between the supply-side pump chamber 1a and a flow route of the supply-side suction port C1 and a flow route of the supply-side discharge port C2 respectively. The check valves (J1 and J2) are openable and closable in accordance with changes in the hydraulic pressure in the supply-side pump chamber 1a that occur with the reciprocating motion of the plunger (N). The check valves (J1 and J2) that are open allow the dialysate to flow therethrough. The check valves (J1 and J2) that are closed block the dialysate from flowing therethrough.

Likewise, the check valves (J3 and J4) are each a valve having a function of preventing the backflow of the dialysate by keeping the dialysate flowing in one specific direction. The check valves (J3 and J4) are each provided between the drain-side pump chamber 1b and a flow route of the drain-side suction port C3 and a flow route of the drain-side discharge port C4 respectively. The check valves (J3 and J4) are openable and closable in accordance with changes in the hydraulic pressure in the drain-side pump chamber 1b that occur with the reciprocating motion of the plunger (N). The check valves (J3 and J4) that are open allow the dialysate to flow therethrough. The check valves (J3 and J4) that are closed block the dialysate from flowing therethrough.

Hence, when the motor (M) is activated, the plunger (N) is displaced in one direction toward an end (a displacement end Sb) of the drain-side pump chamber 1b. In this process, the check valve J1 at the supply-side suction port C1 and the check valve J4 at the drain-side discharge port C4 are opened, whereas the check valve J2 at the supply-side discharge port C2 and the check valve J3 at the drain-side suction port C3 are closed. When the plunger (N) reaches the one end (the displacement end Sb), all of the check valves (J1 to J4) are closed.

Subsequently, the plunger (N) is displaced in the other direction toward an end (a displacement end Sa) of the supply-side pump chamber 1a. In this process, the check valve J2 at the supply-side discharge port C2 and the check valve J3 at the drain-side suction port C3 are opened, whereas the check valve J1 at the supply-side suction port C1 and the check valve J4 at the drain-side discharge port C4 are closed. When the plunger (N) reaches the other end (the displacement end Sa), all of the check valves (J1 to J4) are closed. As the plunger (N) continues to reciprocate, the check valves (J1 to J4) are repeatedly opened and closed as described above.

Thus, the duplex pump 1 (the liquid-delivering device) according to the present embodiment can deliver the liquid by periodically undergoing a suction step in which the liquid (the dialysate to be introduced into the dialyzer 5 or the dialysate as waste liquid to be drained from the dialyzer 5) is taken thereinto (i.e. a suction step of taking the dialysate and the waste liquid into the supply-side pump chamber 1a and the drain-side pump chamber 1b respectively) and a discharge step in which the liquid thus taken is discharged (i.e. a discharge step of discharging the dialysate and the waste liquid taken into the supply-side pump chamber 1a and the drain-side pump chamber 1b respectively).

A control device 7 is, for example, a microcomputer or the like provided in the apparatus body (B) and is capable of controlling operations of devices provided to elements such as the dialysate introduction line L1 and the dialysate drain line L2: specifically, the opening and closing of any of electromagnetic valves, the opening and closing of any of clamps, operations including the activation and stopping of any of actuators such as the duplex pump 1 and the blood pump 4, and operations including the activation and stopping of the ultrafiltration pump 2 at the time of ultrafiltration.

The blood purification apparatus according to the present embodiment illustrated in FIG. 1 includes the ultrafiltration line L3 one end of which is connected to the dialysate introduction line L1 at a position P1 on the downstream side with respect to the duplex pump 1 and the other end of which is connected to the dialysate introduction line L1 at a position P2 on the upstream side with respect to the duplex pump 1. The ultrafiltration line L3 is provided with the ultrafiltration pump 2. That is, the ultrafiltration line L3 forms a flow route extending between the position P1 on the downstream side with respect to the supply-side pump chamber 1a of the duplex pump 1 that is connected to the dialysate introduction line L1 (the position P1 between the supply-side pump chamber 1a and the dialyzer 5) and the position P2 on the upstream side with respect to the supply-side pump chamber 1a, thereby bypassing the supply-side pump chamber 1a of the duplex pump 1.

Figure 5:
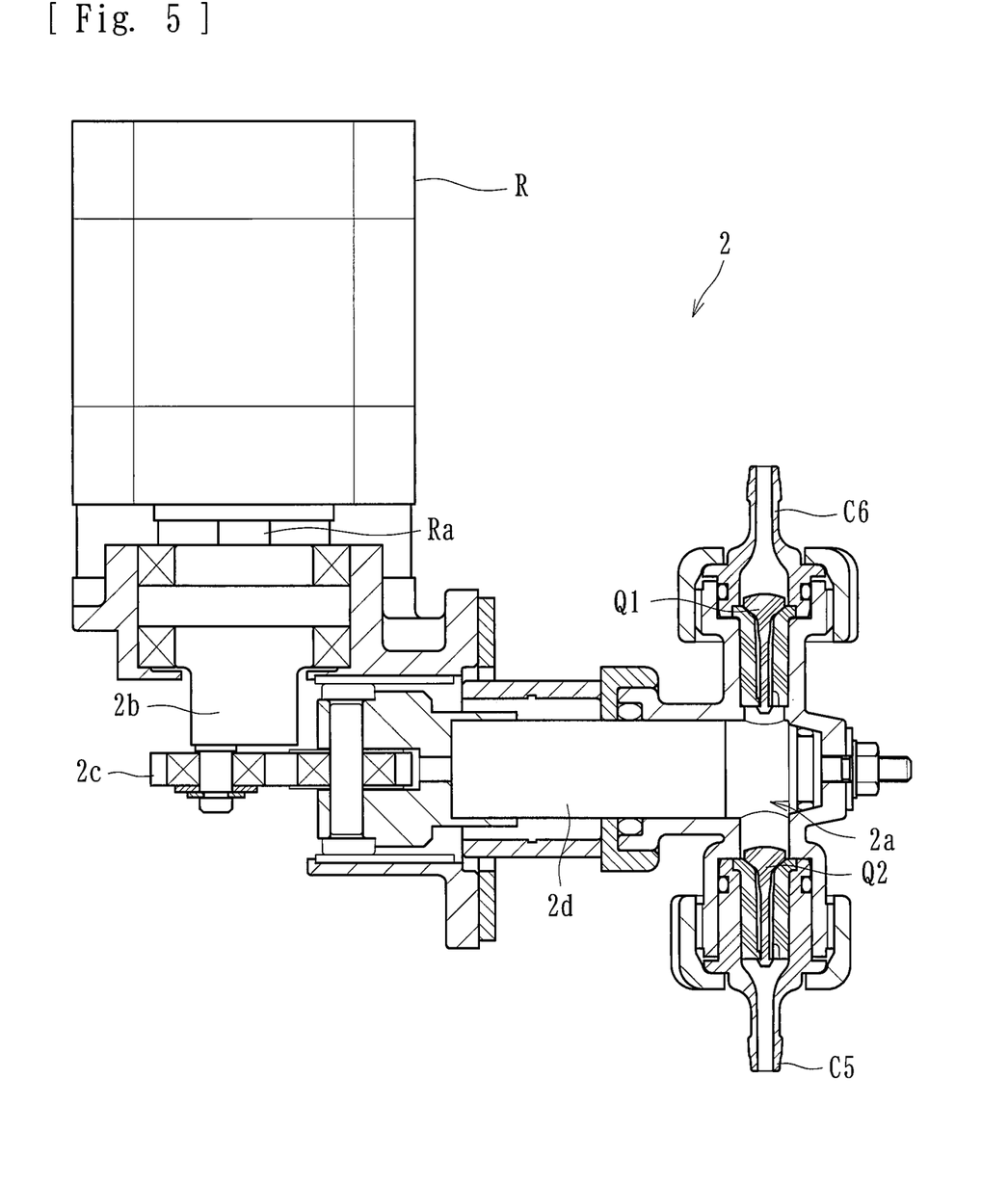
FIG. 5 is a vertical sectional view of an ultrafiltration pump applied to the first and second embodiments of the present invention.

The ultrafiltration pump 2 is capable of removing, through the dialyzer 5, water from the blood flowing through the blood circuit 3. As with the duplex pump 1, the ultrafiltration pump 2 is a pump capable of delivering liquid by periodically undergoing a suction step of taking in the liquid and a discharge step of discharging the taken liquid. More specifically, as illustrated in FIG. 5, the ultrafiltration pump 2 according to the present embodiment includes a pump chamber 2a, a suction port C5 from which the dialysate is allowed to be taken into the pump chamber 2a, a discharge port C6 from which the dialysate in the pump chamber 2a is allowed to be discharged, a motor (R), a cam member 2b, a link mechanism 2c, a plunger 2d, and check valves (Q1 and Q2).

The pump chamber 2a is an accommodation space having a predetermined capacity and allows, with a reciprocating motion of the plunger 2d, the dialysate taken therein from the suction port C5 to flow therethrough and to be discharged from the discharge port C6. The suction port C5 and the discharge port C6 are connected to a pipe forming the ultrafiltration line L3. The plunger 2d operates with the driving force of the motor R that is transmitted thereto through the cam member 2b and the link mechanism 2c, thereby being reciprocatable with respect to the pump chamber 2a. The plunger 2d undergoing the reciprocating motion takes the dialysate into the pump chamber 2a from the suction port C5 and discharges the thus taken dialysate from the discharge port C6, thereby delivering the dialysate.

An output shaft (Ra) of the motor (R) is provided with the cam member 2b. The cam member 2b is provided with the link mechanism 2c. When the motor (R) is activated, the cam member 2b and the link mechanism 2c are actuated to push the plunger 2d in the lengthwise direction and thus causes the plunger 2d to reciprocate in the lateral direction in FIG. 5.

The check valves (Q1 and Q2) are each a valve having a function of preventing the backflow of the dialysate by keeping the dialysate flowing in one specific direction. The check valves (Q1 and Q2) are provided to respective flow routes of the suction port C5 and the discharge port C6. The check valves (Q1 and Q2) are openable and closable in accordance with changes in the hydraulic pressure in the pump chamber 2a that occur with the reciprocating motion of the plunger 2d. The check valves (Q1 and Q2) that are open allow the dialysate to flow therethrough. The check valves (Q1 and Q2) that are closed block the dialysate from flowing therethrough.

Hence, when the motor (R) is activated, the plunger 2d is displaced in one direction. In this process, the check valve Q2 at the suction port C5 is opened, whereas the check valve Q1 at the discharge port C6 is closed. When the plunger 2d reaches one end, both of the check valves (Q1 and Q2) are closed. Subsequently, the plunger 2d is displaced in the other direction. In this process, the check valve Q1 at the discharge port C6 is opened, whereas the check valve Q2 at the suction port C5 is closed.

When the plunger 2d reaches the other end, both of the check valves (Q1 and Q2) are closed. As the plunger 2d continues to reciprocate, the check valves (Q1 and Q2) are repeatedly opened and closed as described above. Thus, the ultrafiltration pump 2 according to the present embodiment can deliver the dialysate by periodically undergoing a suction step of taking in the dialysate and a discharge step of discharging the taken dialysate.

The ultrafiltration pump 2 according to the present embodiment is connected to the ultrafiltration line L3. When activated at the time of ultrafiltration, the ultrafiltration pump 2 draws the dialysate in the dialysate introduction line L1 through the ultrafiltration line L3, thereby making the volume of the dialysate to be introduced into the dialyzer 5 smaller than the volume of the waste liquid to be drained from the dialyzer 5. Thus, ultrafiltration can be implemented.

More specifically, the duplex pump 1 operates such that the volume of the dialysate to be introduced into the dialyzer 5 and the volume of the waste liquid to be drained from the dialyzer 5 are substantially equalized. Therefore, when the ultrafiltration pump 2 is activated and the dialysate flowing toward the dialyzer 5 is drawn through the ultrafiltration line L3, the volume of the dialysate to be introduced into the dialyzer 5 is reduced. Consequently, the volume of the waste liquid to be drained from the dialyzer 5 becomes relatively greater. Hence, water contained in the blood is drained together with the waste liquid by a volume corresponding to the difference from the volume of the dialysate to be introduced into the dialyzer 5. Thus, ultrafiltration is implemented.

In addition, the blood purification apparatus according to the present embodiment is capable of selectively operating in a treatment mode called "ECUM" (extracorporeal ultrafiltration method) (ultrafiltration treatment) in which ultrafiltration alone is performed without causing the dialysate to flow through the dialyzer 5. If the "ECUM" mode is selected, the duplex pump 1 (the liquid-delivering device) and the ultrafiltration pump 2 operate such that the volume of liquid delivery by the duplex pump 1 and the volume of liquid delivery by the ultrafiltration pump 2 are substantially equalized. Therefore, ultrafiltration can be performed without introducing the dialysate into the dialyzer 5.

According to the present embodiment, the ultrafiltration pump 2 is capable of performing ultrafiltration by drawing the dialysate in the dialysate introduction line L1 through the ultrafiltration line L3 such that the volume of the dialysate to be introduced into the dialyzer 5 becomes smaller than the volume of the waste liquid to be drained from the dialyzer 5. Therefore, the waste liquid is prevented from flowing through the ultrafiltration pump 2 during ultrafiltration so that the performance and accuracy of ultrafiltration can be maintained over a long period. In particular, the other end of the ultrafiltration line L3 according to the present embodiment is connected to the dialysate introduction line L1 at a position (the position P2) on the upstream side with respect to the duplex pump 1 (the liquid-delivering device). Therefore, the dialysate drawn through the ultrafiltration line L3 during ultrafiltration can be returned to the dialysate introduction line L1. Thus, the dialysate can be used efficiently.

Furthermore, if the duplex pump 1 (the liquid-delivering device) and the ultrafiltration pump 2 are operated such that the volume of liquid delivery by the duplex pump 1 and the volume of liquid delivery by the ultrafiltration pump 2 are substantially equalized, ultrafiltration can be performed without introducing the dialysate into the dialyzer 5. Therefore, while the waste liquid is prevented from flowing through the ultrafiltration pump 2 so that the performance and accuracy of ultrafiltration can be maintained over a long period, ultrafiltration alone can be performed without introducing the dialysate into the dialyzer 5 (the "ECUM" mode can be selected).

Now, a second embodiment of the present invention will be described.

Figure 2:
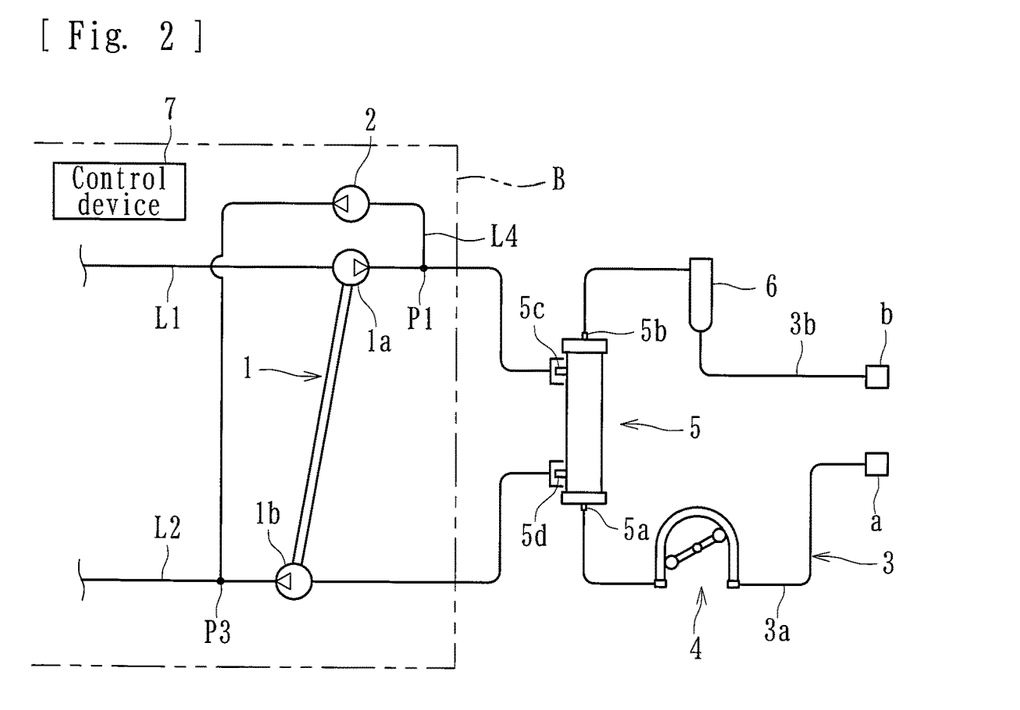
FIG. 2 is a diagram illustrating a blood purification apparatus according to a second embodiment of the present invention.

As with the case of the first embodiment, a blood purification apparatus according to the present embodiment is applied to a hemodialysis apparatus and basically includes, as illustrated in FIG. 2, a blood circuit 3 (including an arterial blood circuit 3a and a venous blood circuit 3b) connected to a dialyzer 5 (a blood purification device), and an apparatus body B including a duplex pump 1 (a liquid-delivering device), an ultrafiltration pump 2, a control device 7, a dialysate introduction line L1, a dialysate drain line L2, and an ultrafiltration line L4. Elements that are the same as those described in the first embodiment are denoted by corresponding ones of the reference numerals, and detailed description of such elements is omitted.

The blood purification apparatus according to the present embodiment illustrated in FIG. 2 includes the ultrafiltration line L4 one end of which is connected to the dialysate introduction line L1 at the position P1 on the downstream side with respect to the duplex pump 1 and the other end of which is connected to the dialysate drain line L2 at a position P3 on the downstream side with respect to the duplex pump 1. The ultrafiltration line L4 is provided with the ultrafiltration pump 2. That is, the ultrafiltration line L4 forms a flow route extending between the position P1 on the downstream side with respect to the supply-side pump chamber 1a of the duplex pump 1 that is connected to the dialysate introduction line L1 (the position P1 between the supply-side pump chamber 1a and the dialyzer 5) and the position P3 on the downstream side with respect to the drain-side pump chamber 1b of the duplex pump 1 that is connected to the dialysate drain line L2.

The ultrafiltration pump 2 is capable of removing, through the dialyzer 5, water from the blood flowing in the blood circuit 3. As with the duplex pump 1, the ultrafiltration pump 2 is a pump capable of delivering liquid by periodically undergoing a suction step of taking in the liquid and a discharge step of discharging the taken liquid. The ultrafiltration pump 2 according to the present embodiment is connected to the ultrafiltration line L4. When activated at the time of ultrafiltration, the ultrafiltration pump 2 draws the dialysate in the dialysate introduction line L1 through the ultrafiltration line L4, thereby making the volume of the dialysate to be introduced into the dialyzer 5 smaller than the volume of the waste liquid to be drained from the dialyzer 5. Thus, ultrafiltration can be implemented.

More specifically, the duplex pump 1 operates such that the volume of the dialysate to be introduced into the dialyzer 5 and the volume of the waste liquid to be drained from the dialyzer 5 are substantially equalized. Therefore, when the ultrafiltration pump 2 is activated and the dialysate flowing toward the dialyzer 5 is drawn through the ultrafiltration line L4, the volume of the dialysate to be introduced into the dialyzer 5 is reduced. Consequently, the volume of the waste liquid to be drained from the dialyzer 5 becomes relatively greater. Hence, water contained in the blood is drained together with the waste liquid by a volume corresponding to the difference from the volume of the dialysate to be introduced into the dialyzer 5. Thus, ultrafiltration is implemented.

In addition, as with the case of the first embodiment, the blood purification apparatus according to the present embodiment is capable of selectively operating in a treatment mode called "ECUM" (extracorporeal ultrafiltration method) (ultrafiltration treatment) in which ultrafiltration alone is performed without causing the dialysate to flow through the dialyzer 5. If the "ECUM" mode is selected, the duplex pump 1 (the liquid-delivering device) and the ultrafiltration pump 2 operate such that the volume of liquid delivery by the duplex pump 1 and the volume of liquid delivery by the ultrafiltration pump 2 are substantially equalized. Therefore, ultrafiltration can be performed without introducing the dialysate into the dialyzer 5. In the treatment performed in the "ECUM" mode, diffusion with the dialyzer 5 is not performed, and the removal of solutes from the blood is avoided. Consequently, the drop in blood pressure can be suppressed.

According to the present embodiment, the ultrafiltration pump 2 is capable of performing ultrafiltration by drawing the dialysate in the dialysate introduction line L1 through the ultrafiltration line L4, thereby making the volume of the dialysate to be introduced into the dialyzer 5 smaller than the volume of the waste liquid to be drained from the dialyzer 5. Therefore, the waste liquid is prevented from flowing through the ultrafiltration pump 2 during ultrafiltration so that the performance and accuracy of ultrafiltration can be maintained over a long period. In particular, the other end of the ultrafiltration line L4 according to the present embodiment is connected to the dialysate drain line L2 at a position (the position P3) on the downstream side with respect to the duplex pump 1 (the liquid-delivering device). Therefore, the dialysate drawn through the ultrafiltration line L4 during ultrafiltration can be drained to the outside of the apparatus through the dialysate drain line L2.

Furthermore, if the duplex pump 1 (the liquid-delivering device) and the ultrafiltration pump 2 are operated such that the volume of liquid delivery by the duplex pump 1 and the volume of liquid delivery by the ultrafiltration pump 2 are substantially equalized, ultrafiltration can be performed without introducing the dialysate into the dialyzer 5. Therefore, while the waste liquid is prevented from flowing through the ultrafiltration pump 2 so that the performance and accuracy of ultrafiltration can be maintained over a long period, ultrafiltration alone can be performed without introducing the dialysate into the dialyzer 5 (the "ECUM" mode can be selected).

Figure 6:
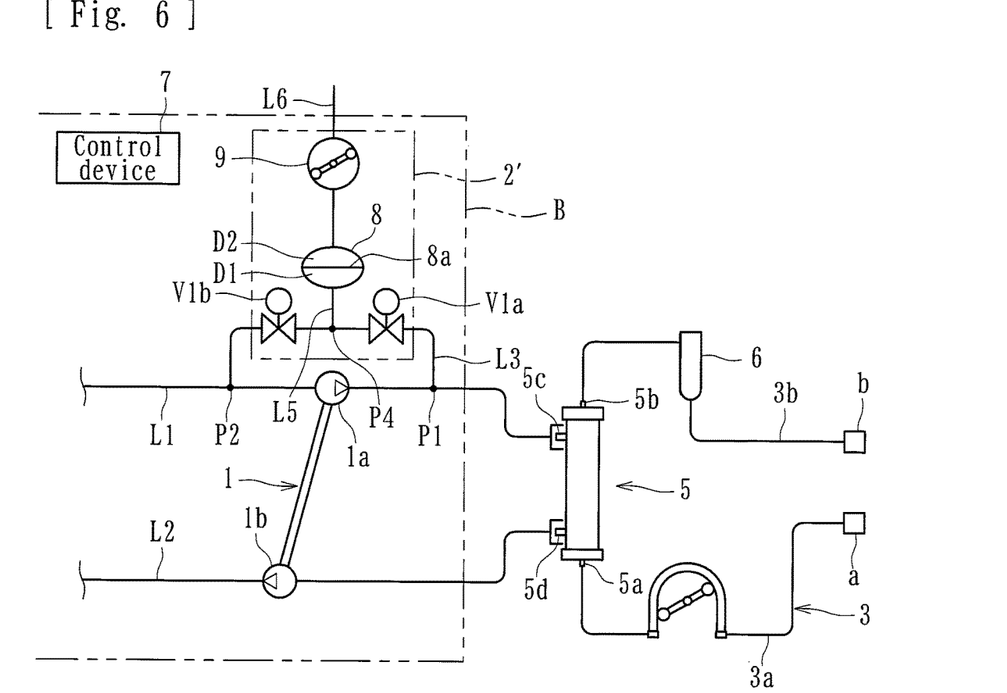
FIG. 6 is a diagram illustrating an ultrafiltration pump according to another embodiment applied to the blood purification apparatus.
Figure 7:
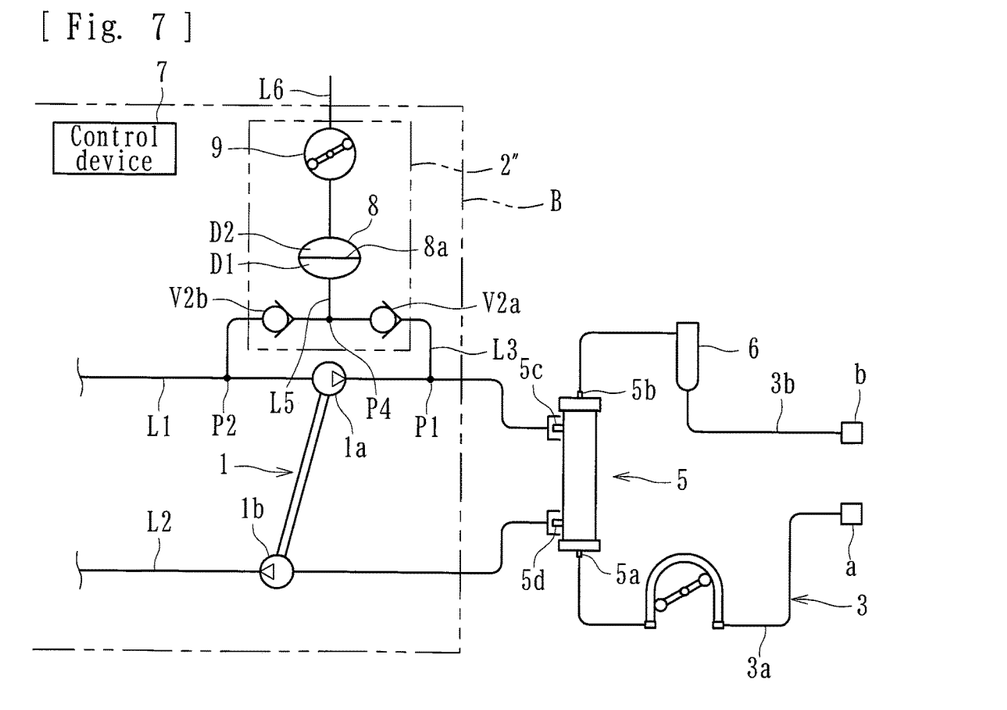
FIG. 7 is a diagram illustrating an ultrafiltration pump according to yet another embodiment applied to the blood purification apparatus.

The ultrafiltration pump 2 according to each of the first and second embodiments may be replaced with an ultrafiltration pump 2' illustrated in FIG. 6 or an ultrafiltration pump 2" illustrated in FIG. 7. As illustrated in FIGS. 6 and 7, the ultrafiltration pumps 2' and 2" each include a chamber 8 having compartments D1 and D2 separated from each other by a diaphragm 8a, an air pump 9 such as a peristaltic pump or a diaphragm pump, a flow route L5 one end of which is connected to the ultrafiltration line L3 and the other end of which is connected to the compartment D1 of the chamber 8, and a flow route L6 provided with the air pump 9 and one end of which is connected to the compartment D2 of the chamber 8. The other end of the flow route L6 is open to the atmosphere. The ultrafiltration pumps 2' and 2" are each connected to the ultrafiltration line L3 according to the first embodiment but may each be connected to the ultrafiltration line L4 according to the second embodiment.

The ultrafiltration pump 2' is connected to the ultrafiltration line L3 and is provided with, as illustrated in FIG. 6, an electromagnetic valve V1a (or another clamping device) at a position on the upstream side (the right side in the drawing) with respect to a position P4 where the ultrafiltration line L3 is connected to the flow route L5, and an electromagnetic valve V1b (or another clamping device) at a position on the downstream side (the left side in the drawing) with respect to the position P4. When the ultrafiltration pump 2' is activated, the electromagnetic valve V1a is opened, whereas the electromagnetic valve V1b is closed. Furthermore, the air pump 9 releases air in the compartment D2 to the atmosphere. Consequently, the dialysate at the position P1 is introduced into the compartment D1.

Subsequently, when the compartment D1 is filled with the dialysate (or when the amount of dialysate exceeds a predetermined level), the electromagnetic valve V1a is closed, whereas the electromagnetic valve V1b is opened. Furthermore, the air pump 9 sends air into the compartment D2. Consequently, the dialysate in the compartment D1 is delivered to the position P2. As the above process is repeated, the dialysate in the dialysate introduction line L1 can be drawn through the ultrafiltration line L3. Accordingly, the volume of the dialysate to be introduced into the dialyzer 5 can be made smaller than the volume of the waste liquid to be drained from the dialyzer 5. Thus, ultrafiltration can be implemented.

The ultrafiltration pump 2" is connected to the ultrafiltration line L3 and is provided with, as illustrated in FIG. 7, a check valve V2a at a position on the upstream side (the right side in the drawing) with respect to the position P4 where the ultrafiltration line L3 is connected to the flow route L5, and a check valve V2b at a position on the downstream side (the left side in the drawing) with respect to the position P4. When the ultrafiltration pump 2" is activated, the air pump 9 releases air in the compartment D2 to the atmosphere. Consequently, the dialysate at the position P1 is introduced into the compartment D1. In this state, the check valve V2a allows liquid to flow therethrough, whereas the check valve V2b blocks liquid from flowing therethrough.

Subsequently, when the compartment D1 is filled with the dialysate (or when the amount of dialysate exceeds a predetermined level), the air pump 9 sends air into the compartment D2. Consequently, the dialysate in the compartment D1 is delivered to the position P2. In this state, the check valve V2a blocks liquid from flowing therethrough, whereas the check valve V2b allows liquid to flow therethrough. As the above process is repeated, the dialysate in the dialysate introduction line L1 can be drawn through the ultrafiltration line L3. Accordingly, the volume of the dialysate to be introduced into the dialyzer 5 can be made smaller than the volume of the waste liquid to be drained from the dialyzer 5. Thus, ultrafiltration can be implemented.

Now, a method of preventing the backflow of the dialysate from the dialyzer 5 into the dialysate introduction line L1 in the blood purification apparatus including the ultrafiltration line L3 or L4 as in the first or second embodiment will be described.

As described above, the duplex pump 1 (or the ultrafiltration pump 2) in this case is a pump capable of delivering liquid by periodically undergoing a suction step of taking in the liquid and a discharge step of discharging the taken liquid, and is capable of delivering the liquid while maintaining the volume of liquid (dialysate) discharge in the discharge step at a predetermined level by increasing the pressure of liquid discharge in an early stage and in a late stage of the discharge step while reducing the pressure of liquid discharge in an intermediate stage between the two stages.

Figure 8:
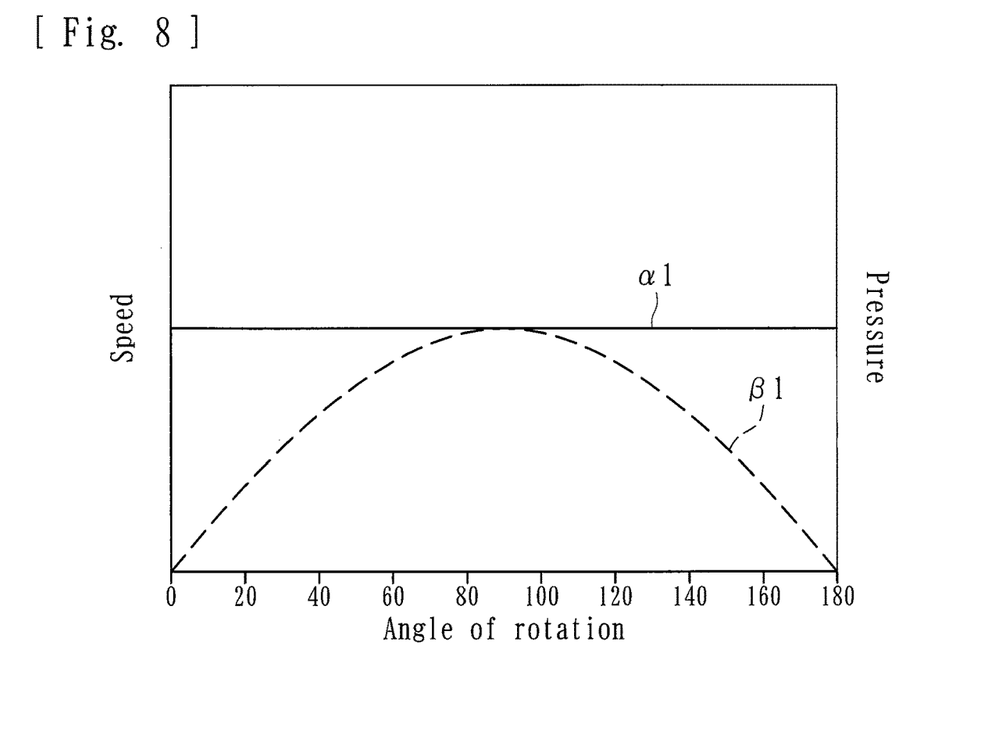
FIG. 8 is a graph illustrating a relationship between the operating speed of a plunger and the discharge pressure in the duplex pump (liquid-delivering device) of the blood purification apparatus that undergoes a discharge step accompanied by no control operation for backflow prevention.

For example, when the motor M (see FIG. 3) is activated normally (a case of a graph α1 where the operating speed is constant), as illustrated in FIG. 8, the discharge pressure generated in the discharge step undergone by the duplex pump 1 changes with the angle of rotation of the motor M in such a manner as to form a gentle parabolic curve as represented by a graph β1. In such a case, the discharge pressure of the duplex pump 1 stays low for a relatively long period. If the ultrafiltration pump 2 undergoes the suction step while the discharge pressure of the duplex pump 1 is low and if the suction pressure of the ultrafiltration pump 2 is greater than the discharge pressure of the duplex pump 1, the dialysate flows backward from the dialyzer 5. Note that, in the drawing, the graph α1 represents changes in speed (speed of rotation), and the graph β1 represents changes in pressure.

Figure 9:
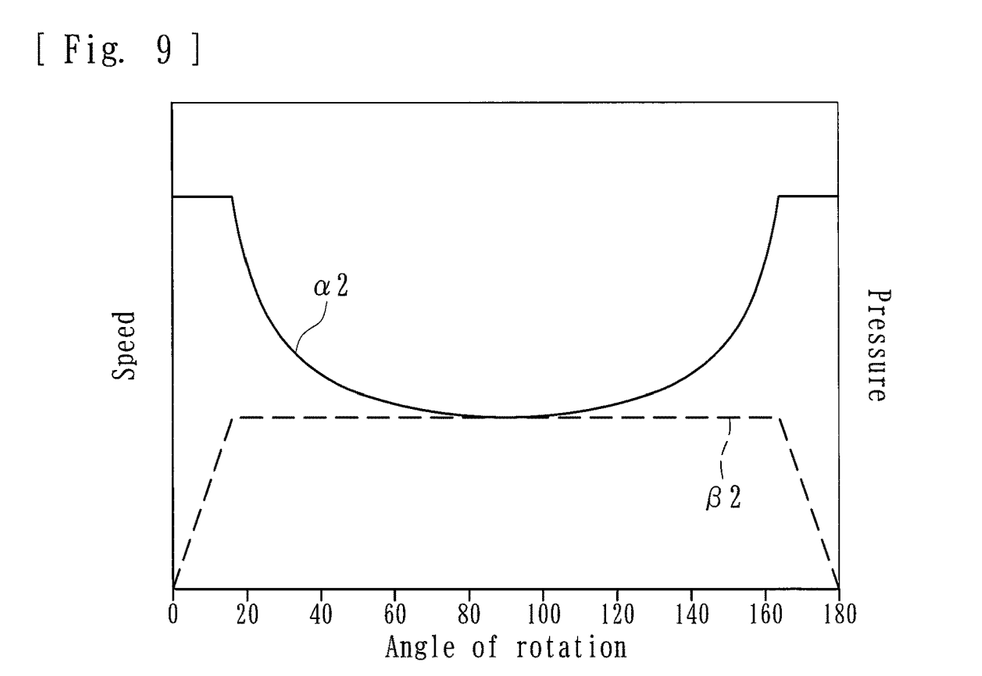
FIG. 9 is a graph illustrating a relationship between the operating speed of the plunger and the discharge pressure in the duplex pump (liquid-delivering device) of the blood purification apparatus that undergoes a discharge step accompanied by a control operation for backflow prevention.

To avoid the backflow, the present embodiment employs a method illustrated in FIG. 9 in which the operating speed of the motor (M) is increased (the speed of the plunger (N) is made relatively high) as represented by a graph α2 in the early stage (a period from the start to a point after a predetermined time from the start) and in the late stage (a period from a point before a predetermined time from the end to the end) of the discharge step undergone by the duplex pump 1, whereas the operating speed of the motor (M) is reduced (the speed of the plunger (N) is made relatively low) in the intermediate stage. Note that, in the drawing, a graph α2 represents changes in speed (speed of rotation), and the graph β2 represents changes in pressure.

As represented by the graph β2, since the pressure of liquid discharge is increased in the early stage and in the late stage of the discharge step but is reduced in the intermediate stage, the liquid can be delivered while the volume of liquid discharge in the discharge step is maintained at a predetermined level. Such a configuration can reduce the probability that the ultrafiltration pump 2 may undergo the suction step while the discharge pressure in the discharge step undergone by the duplex pump 1 (the liquid-delivering device) is low. Accordingly, the probability that the dialysate introduced into the blood purification device flows backward into the dialysate introduction line L1 can be reduced.

Now, another method of preventing the backflow of the dialysate from the dialyzer 5 into the dialysate introduction line L1 in the blood purification apparatus including the ultrafiltration line L3 or L4 as in the first or second embodiment will be described.

As described above, the duplex pump 1 (and the ultrafiltration pump 2) in this case is a pump capable of delivering liquid by periodically undergoing a suction step of taking in the liquid and a discharge step of discharging the taken liquid. Furthermore, as illustrated in FIGS. 10 and 11, the ultrafiltration pump 2 operates (is electrically turned on) only in a period (T) where the duplex pump 1 is undergoing the discharge step.

Figure 10:
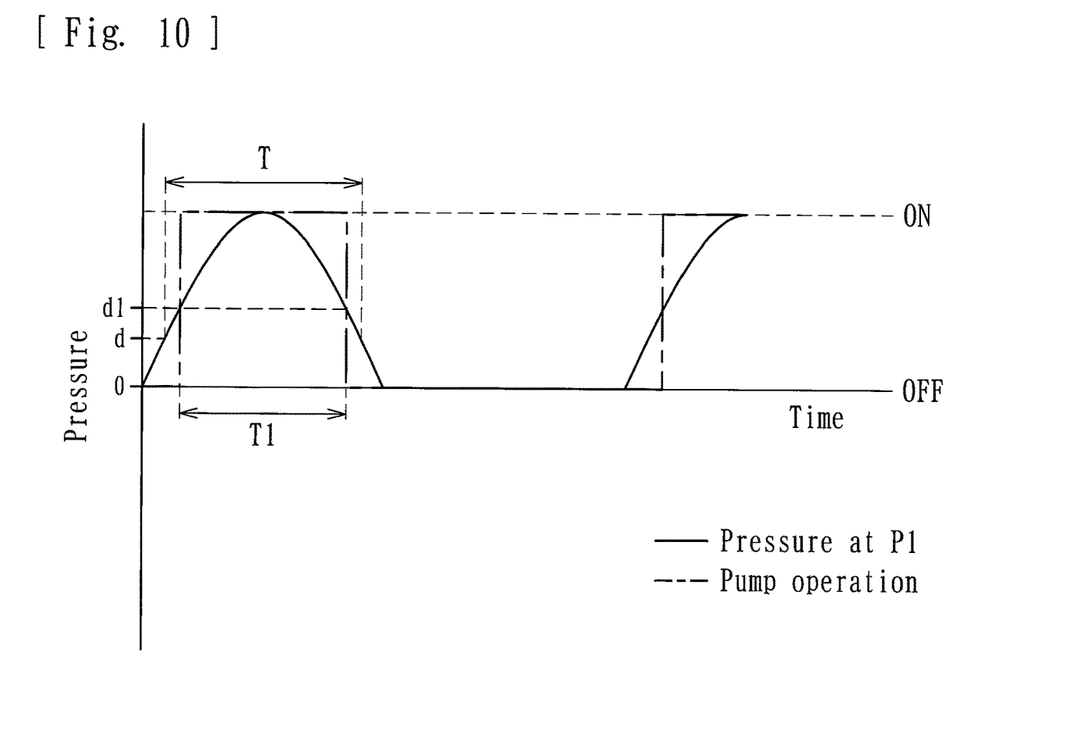
FIG. 10 is a graph illustrating the timing of operation of the ultrafiltration pump (at a high ultrafiltration rate) operating with the duplex pump (liquid-delivering device) of the blood purification apparatus that undergoes another control operation for backflow prevention.
Figure 11:
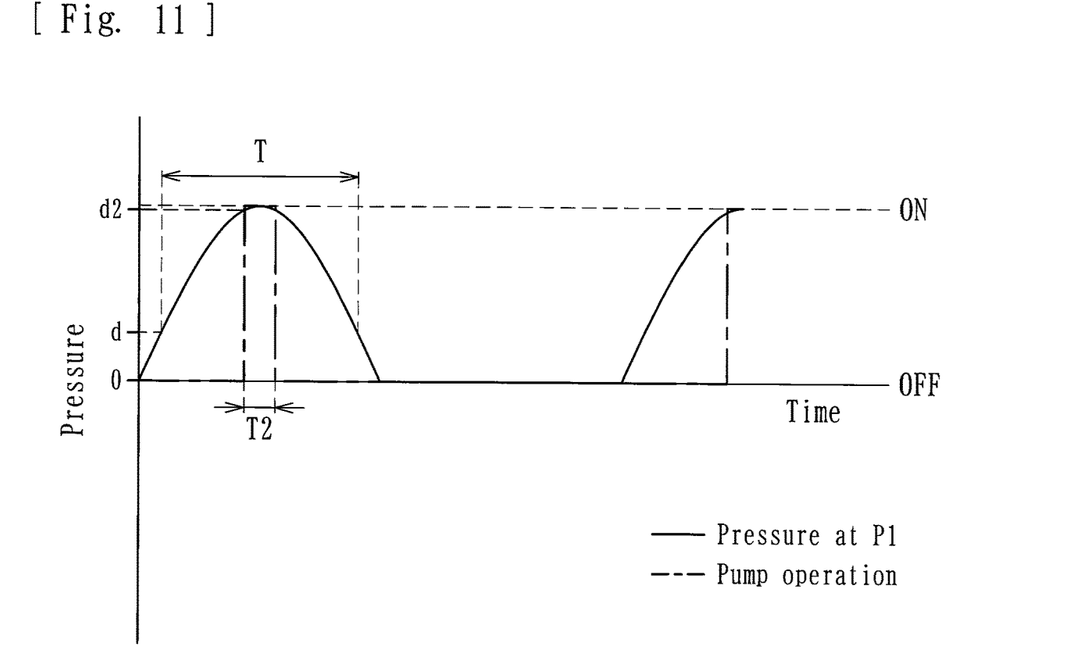
FIG. 11 is a graph illustrating the timing of operation of the ultrafiltration pump (at a low ultrafiltration rate) operating with the duplex pump (liquid-delivering device) of the blood purification apparatus that undergoes the other control operation for backflow prevention.

In particular, in the backflow-preventing method according to the present embodiment, the ultrafiltration pump 2 operates on condition that the pressure of liquid (dialysate) discharge in the discharge step undergone by the duplex pump 1 (the liquid-delivering device) exceeds a predetermined value ("d" in FIGS. 10 and 11). For example, when the ultrafiltration rate is high, as illustrated in FIG. 10, the ultrafiltration pump 2 operates within the period T where the discharge pressure of the duplex pump 1 (the pressure at the position P1 illustrated in FIGS. 1, 2) is higher than the value d, particularly over a period T1 where the discharge pressure (the pressure at the position P1) is higher than a value d1. When the ultrafiltration rate is low, as illustrated in FIG. 11, the ultrafiltration pump 2 operates within the period T where the discharge pressure of the duplex pump 1 (the pressure at the position P1 illustrated in FIGS. 1, 2) is higher than the value d, particularly over a period T2 where the discharge pressure (the pressure at the position P1) is higher than a value d2 (d1<d2).

In the backflow-preventing method according to the present embodiment, the ultrafiltration pump 2 operates only in the period where the duplex pump 1 (the liquid-delivering device) is undergoing the discharge step. Therefore, activation of the ultrafiltration pump 2 while the duplex pump 1 is undergoing the suction step can be assuredly avoided. Accordingly, the dialysate introduced into the dialyzer 5 (the blood purification device) can be prevented from flowing backward into the dialysate introduction line L1. In particular, if the ultrafiltration pump 2 is operated on condition that the pressure of liquid discharge in the discharge step undergone by the duplex pump 1 exceeds a predetermined value, the dialysate introduced into the dialyzer 5 can be more assuredly prevented from flowing backward into the dialysate introduction line L1.

Now, yet another method of preventing the backflow of the dialysate from the dialyzer 5 into the dialysate introduction line L1 in the blood purification apparatus including the ultrafiltration line L3 or L4 as in the first or second embodiment will be described.

As described above, the duplex pump 1 (the liquid-delivering device) and the ultrafiltration pump 2 in this case include the respective plungers ((N) and 2d) with which the suction step and the discharge step are implemented. Furthermore, the blood purification apparatus includes a synchronization device (not illustrated) that couples the plunger (N) of the duplex pump 1 and the plunger 2d of the ultrafiltration pump 2 to each other for synchronous operation with the aid of elements such as a cam and a link. Furthermore, the synchronization device operates such that the ultrafiltration pump 2 undergoes the suction step while the duplex pump 1 is undergoing the discharge step, and the ultrafiltration pump 2 undergoes the discharge step while the duplex pump 1 is undergoing the suction step.

Figure 12:
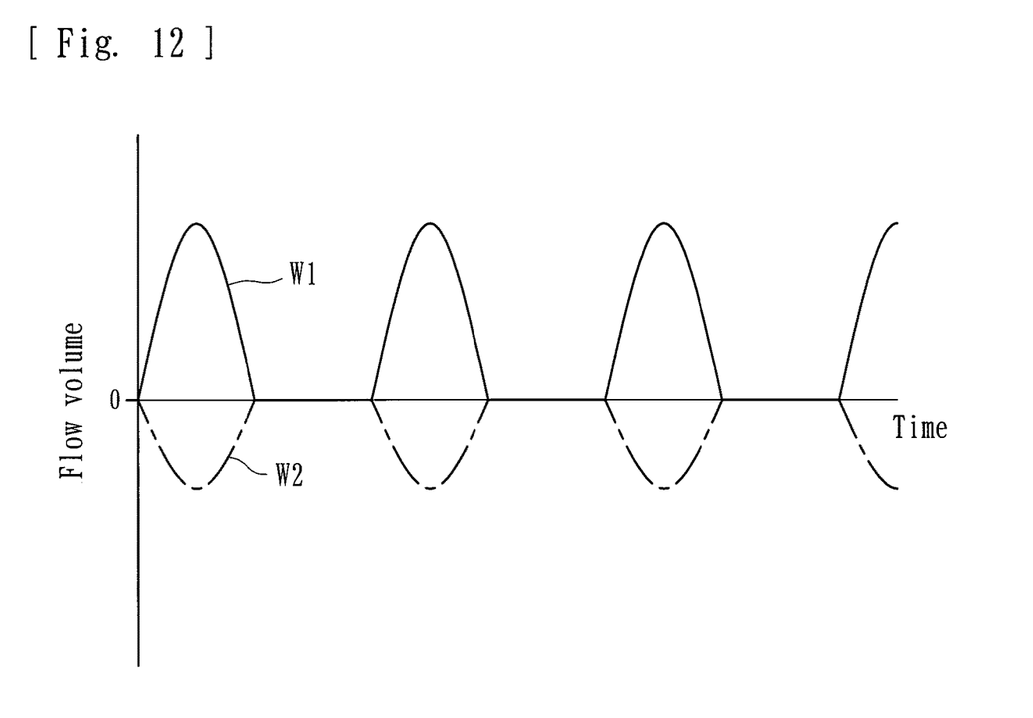
FIG. 12 is a graph illustrating the timing of operation of the ultrafiltration pump (synchronized with the duplex pump) operating with the duplex pump (liquid-delivering device) of the blood purification apparatus that undergoes another control operation for backflow prevention.

For example, in FIG. 12 where the horizontal axis represents time while the vertical axis represents the flow volume of the dialysate at the position P1, the change in the flow volume of the duplex pump 1 is graphed as W1, and the change in the flow volume of the ultrafiltration pump 2 is graphed as W2. In this case, the synchronization device operates such that the ultrafiltration pump 2 undergoes the suction step while the duplex pump 1 is undergoing the discharge step, and the ultrafiltration pump 2 undergoes the discharge step while the duplex pump 1 is undergoing the suction step. In the drawing, a part of the vertical axis above the point 0 represents the volume of the flow from the position P1 toward the dialyzer 5, and a part of the vertical axis below the point 0 represents the volume of the flow from the position P1 toward the ultrafiltration line L3.

In this method, the ultrafiltration pump 2 can be assuredly prevented from undergoing the discharge step while the duplex pump 1 (the liquid-delivering device) is undergoing the suction step. Accordingly, the dialysate introduced into the dialyzer 5 (the blood purification device) can be much more assuredly prevented from flowing backward into the dialysate introduction line L1. The synchronization device is not limited to a device that physically couples the plungers with elements such as a cam and a link, and may be a device that electrically controls the plungers to operate synchronously.

According to the above embodiment, the liquid-delivering device is the duplex pump 1 that includes the supply-side pump chamber 1a connected to the dialysate introduction line L1 and being capable of accommodating and discharging the dialysate from and into the dialysate introduction line L1, and the drain-side pump chamber 1b connected to the dialysate drain line L2 and being capable of taking in and accommodating the waste liquid from the dialysate drain line L2. Furthermore, the liquid-delivering device delivers the liquid such that the volume of discharge from the supply-side pump chamber 1a and the volume of suction into the drain-side pump chamber 1b are substantially equalized. Furthermore, one end of the ultrafiltration line (L3 or L4) is connected to the dialysate introduction line L1 at a position between the supply-side pump chamber 1a and the point of connection of the dialysate introduction line L1 to the dialyzer 5 (the blood purification device). Therefore, while the dialysate and the waste liquid are delivered by the duplex pump 1, the waste liquid is prevented from flowing through the ultrafiltration pump during ultrafiltration so that the performance and accuracy of ultrafiltration can be maintained over a long period.

While some embodiments have been described above, the present invention is not limited thereto. For example, as long as one end of the ultrafiltration line (L3 or L4) is connected to the dialysate introduction line L1 at a position on the downstream side with respect to the duplex pump 1 (the liquid-delivering device), the other end of the ultrafiltration line (L3, L4) may be connected to a position other than the dialysate introduction line L1 or the dialysate drain line L2 (for example, the dialysate may be discharged directly to the outside of the apparatus body (B)). Moreover, while the duplex pump 1 (the liquid-delivering device) and the ultrafiltration pump 2 according to any of the above embodiments are each a pump capable of delivering liquid by periodically undergoing a suction step of taking in the liquid and a discharge step of discharging the taken liquid, one of or both of the two may skip the suction step and the discharge step in delivering the liquid.

The present invention is applicable to any blood purification apparatus, including those having other additional functions and so forth, as long as the following are satisfied: the blood purification apparatus includes an ultrafiltration line one end of which is connected to a dialysate introduction line at a position on the downstream side with respect to a liquid-delivering device, the ultrafiltration line is provided with an ultrafiltration pump, and the ultrafiltration pump is capable of performing ultrafiltration by drawing dialysate in the dialysate introduction line through the ultrafiltration line such that the volume of the dialysate to be introduced into a blood purification device becomes smaller than the volume of waste liquid to be drained from the blood purification device.

REFERENCE SIGNS 1 duplex pump (liquid-delivering device)
1a supply-side pump chamber
1b drain-side pump chamber
2 ultrafiltration pump
2a pump chamber
2b cam member
2c link mechanism
2d plunger 3 blood circuit
3a arterial blood circuit
3b venous blood circuit
4 blood pump
5 dialyzer (blood purification device)
6 air-trap chamber
7 control device
8 chamber
9 air pump
B apparatus body
L1 dialysate introduction line
L2 dialysate drain line
L3 ultrafiltration line
L4 ultrafiltration line
M motor
Ma output shaft
R motor
Ra output shaft
E cam member
Ea cam portion
N plunger
Na recess
K block slider
J1 to J4 check valve
Q1, Q2 check valve
C1 supply-side suction port
C2 supply-side discharge port
C3 drain-side suction port
C4 drain-side discharge port
C5 suction port
C6 discharge port

The invention claimed is:

1. A blood purification apparatus comprising:
a blood circuit including an arterial blood circuit and a venous blood circuit and through which blood of a patient is allowed to extracorporeally circulate;
a blood purification device connected to the arterial blood circuit and to the venous blood circuit and that purifies the blood circulating through the blood circuit;
a dialysate introduction line that allows dialysate to be introduced into the blood purification device;
a dialysate drain line that allows waste liquid to be drained from the blood purification device;
a liquid-delivering device extending between and connecting the dialysate introduction and the dialysate drain line, wherein the liquid-delivering device is capable of delivering liquid such that a volume of the dialysate to be introduced into the blood purification device and a volume of the waste liquid to be drained from the blood purification device are substantially equalized;
an ultrafiltration pump capable of removing, through the blood purification device, water from the blood circulating through the blood circuit,
an ultrafiltration line comprising:
a first end of the ultrafiltration line connected to the dialysate introduction line at a position on a downstream side with respect to the liquid-delivering device and
a second end of the ultrafiltration line connected to the dialysate introduction line at a position on an upstream side of the liquid-delivering device with the ultrafiltration pump located between the first end and the second end, and
a control device in communication with the ultrafiltration pump and the liquid-delivering device;
wherein the ultrafiltration line is connected with the ultrafiltration pump and the ultrafiltration pump is controllable by the control device to perform ultrafiltration by drawing the dialysate in the dialysate introduction line through the ultrafiltration line and the control device is configured to control the ultrafiltration pump so that the volume of the dialysate to be introduced into the blood purification device becomes smaller than the volume of the waste liquid to be drained from the blood purification device;
wherein the liquid-delivering device and the ultrafiltration pump are in communication with the control device and the control device activates the liquid-delivering device and the ultrafiltration pump so that each are capable of delivering liquid by periodically causing suction to take in the liquid and discharge to move out the liquid;
wherein the control device is configured to control the ultrafiltration pump to operate only in a period when the liquid-delivering device is undergoing the discharge, and
wherein the control device is operable to control the ultrafiltration pump so that a pressure of liquid discharge during the discharge by the liquid-delivering device exceeds a predetermined value so that the dialysate is prevented from flowing backwards.

2. The blood purification apparatus according to claim 1, wherein the liquid-delivering device and the ultrafiltration pump moves a volume of the liquid so that the volume of the liquid moved by the liquid-delivering device and the ultrafiltration pump are substantially equalized so that ultrafiltration is capable of being performed with an introduction of dialysate into the blood purification device.

3. The blood purification apparatus according to claim 1, wherein the blood purification apparatus includes a synchronization device capable of synchronizing the taking in of the liquid and discharging the liquid by the liquid-delivering device and the ultrafiltration pump such that the ultrafiltration pump undergoes the taking in of the liquid while the liquid-delivering device is undergoing the discharging, and the ultrafiltration pump undergoes the discharge while the liquid-delivering device is undergoing the taking in of the liquid.

4. The blood purification apparatus according to claim 3, wherein the liquid-delivering device or the ultrafiltration pump is a pump capable of delivering the liquid by periodically taking in the liquid and discharging the taken liquid, and the pump is capable of delivering the liquid while maintaining a volume of the liquid a predetermined level by increasing a pressure of liquid discharge in a first stage and in a third stage of discharging while reducing the pressure of the liquid discharge in a second stage between the first stage and the third stage.

5. The blood purification apparatus according to claim 3, wherein the synchronization device includes synchronization plungers and the ultrafiltration pump includes ultrafiltration plungers, wherein the synchronization device synchronizes the synchronization plungers and the ultrafiltration plungers.

6. The blood purification apparatus according to claim 1, wherein the liquid-delivering device or the ultrafiltration pump is a pump capable of delivering the liquid by periodically taking in the liquid and discharging the taken liquid, and the pump is capable of delivering the liquid while maintaining a volume of liquid at a predetermined level by increasing a pressure of the liquid discharge in a first stage and in a third stage of discharging while reducing the pressure of the liquid discharge in a second stage between the first stage and the third stage.

7. The blood purification apparatus according to claim 1, wherein the liquid-delivering device is a duplex pump that includes a supply-side pump chamber connected to the dialysate introduction line and being capable of accommodating and discharging the dialysate from and into the dialysate introduction line, and a drain-side pump chamber connected to the dialysate drain line and being capable of taking in and accommodating the waste liquid from the dialysate drain line; wherein the liquid-delivering device delivers the liquid such that a volume of discharge from the supply-side pump chamber and a volume of suction into the drain-side pump chamber are substantially equalized; and wherein one end of the ultrafiltration line is connected to the dialysate introduction line at a position between the supply-side pump chamber and a point of connection of the dialysate introduction line to the blood purification device.

8. The blood purification apparatus according to claim 1, wherein when the liquid-delivering device and the ultrafiltration pump move a volume of the liquid that are substantially equalized, ultrafiltration is capable of being performed by introducing dialysate into the blood purification device.

9. The blood purification apparatus according to claim 8, wherein the blood purification apparatus includes a synchronization device capable of synchronizing taking in the liquid and the discharge undergone by the liquid-delivering device and the ultrafiltration pump such that the ultrafiltration pump undergoes the taking in of the liquid while the liquid-delivering device is undergoing the discharge, and the ultrafiltration pump undergoes the discharge while the liquid-delivering device is undergoing the taking in of the liquid.

10. The blood purification apparatus according to claim 8, wherein the liquid-delivering device or the ultrafiltration pump is a pump capable of delivering the liquid by periodically taking in the liquid and discharging the taken liquid, and the pump is capable of delivering the liquid while maintaining a volume of liquid discharge at a predetermined level by increasing a pressure of the liquid discharge in first stage and in a third stage of discharging while reducing the pressure of the liquid discharge in a second stage between the first stage and the third stage.

11. The blood purification apparatus according to claim 1, wherein the control device is operable to control ultrafiltration without introducing the dialysate into the blood purification device when the liquid-delivering device and the ultrafiltration pump are operated such that a volume of the liquid delivery by the liquid-delivering device and a volume of the liquid delivery by the ultrafiltration pump are substantially equalized.

12. The blood purification apparatus according to claim 1, wherein the liquid-delivering device is a duplex pump that includes a supply-side pump chamber connected to the dialysate introduction line and being capable of accommodating and discharging the dialysate from and into the dialysate introduction line, and a drain-side pump chamber connected to the dialysate drain line and being capable of taking in and accommodating the waste liquid from the dialysate drain line; wherein the liquid-delivering device delivers the liquid such that a volume of discharge from the supply-side pump chamber and a volume of suction into the drain-side pump chamber are substantially equalized; and wherein one end of the ultrafiltration line is connected to the dialysate introduction line at a position between the supply-side pump chamber and a point of connection of the dialysate introduction line to the blood purification device.

13. The blood purification apparatus according to claim 1, wherein the liquid-delivering device is a duplex pump with a motor, wherein the motor has an angle of rotation that generates a variable discharge pressure.

14. The blood purification apparatus according to claim 13, wherein when a suction pressure of the duplex pump is greater than a discharg pressure of the ultrafiltration pump, the dialysate flows backwards from a dialyzer.

15. The blood purification apparatus according to claim 13, wherein the control device controls a speed of the motor so that the speed of the motor has a first stage, a second stage, and a third stage.

16. The blood purification apparatus according to claim 15, wherein a discharge pressure increases in the first stage until the second stage is reached and wherein the discharge pressure decreases in the third stage.

17. The blood purification apparatus according to claim 1, wherein the blood purification apparatus includes a synchronization device capable of synchronizing the suction and the discharge undergone by the liquid-delivering device and the ultrafiltration pump such that the ultrafiltration pump undergoes the suction while the liquid-delivering device is undergoing the discharge, and the ultrafiltration pump undergoes the discharge while the liquid-delivering device is undergoing the suction.

* * * * *